US006383808B1

United States Patent
Monia et al.

(10) Patent No.: US 6,383,808 B1
(45) Date of Patent: May 7, 2002

(54) ANTISENSE INHIBITION OF CLUSTERIN EXPRESSION

(75) Inventors: Brett P. Monia, La Costa; Susan M. Freier, San Diego, both of CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/659,791

(22) Filed: Sep. 11, 2000

(51) Int. Cl.$^7$ ............................................. C12N 5/00
(52) U.S. Cl. ..................... 435/375; 435/325; 435/6; 435/91.1; 536/24.5; 536/24.3; 536/24.31; 536/24.33
(58) Field of Search .......................... 435/6, 91.1, 91.2, 435/91.3, 325, 375; 536/23.1, 23.2, 24.5, 24.33, 24.31, 24.3; 514/44

(56) References Cited

U.S. PATENT DOCUMENTS

| | | | |
|---|---|---|---|
| 5,695,995 A | * | 12/1997 | Weintraub et al. |
| 5,739,310 A | * | 4/1998 | Yao et al. |
| 5,786,213 A | * | 7/1998 | Singh et al. |
| 5,801,154 A | * | 9/1998 | Baracchini et al. |
| 5,945,290 A | * | 8/1999 | Cowsert |
| 5,948,680 A | * | 9/1999 | Baker et al. |
| 5,958,773 A | * | 9/1999 | Monia et al. |
| 5,959,097 A | * | 9/1999 | Monia et al. |

FOREIGN PATENT DOCUMENTS

| | | |
|---|---|---|
| WO | WO 95/16916 | 6/1995 |
| WO | WO 00/49937 A3 | 8/2000 |

OTHER PUBLICATIONS

Kang et al., Antisense Oligonucleotide of Clusterin mRNA Induces Apoptotic Cell Death and Prevents Adhesion of Rat ASC–170 Sertoli Cells, Dec. 1999, Molecules and Cells, vol. 10, No. 2, pp. 193–198.*
Miyake et al, Antisense TRPM–2 Oligodeoxynucleotides Chemosensitize Human Androgen–independent PC–3 Prostate Cancer Cells Both in Vitro and in Vivo, May 2000, Clinical Cancer Research, vol. 6, pp. 1655–1663.*
Zwain et al, Clusterin Protects Granulosa Cells from Apoptotic Cell Death during Follicular Atresia, Mar. 2000, Experimental Cell Research, vol. 257, pp. 101–110.*
Stanley T. Crooke, Antisense Research and Application, Jul. 1998, Springer, pp. 1–51.*
Sudhir Agrawal, Antisense Oligonucleotides: towards clinical trials, Oct. 1996, Tibtech, vol. 14, pp. 376–387.*
Wong et al, Molecular Characterization of Human TRPM–2/ clusterin, a Gene Associated with Sperm Maturation, Apoptosis and Neurodegeneration, Feb. 1994, Eur. J. Biochem., pp. 917–925.*
Andrea D. Branch, A good Antisense Molecule is Hard to Find, Feb. 1998, TIBS 23, pp. 45–50.*

Bailey et al., Clusterin in the male reproductive system: localization and possible function, *Mol. Cell. Endocrinol.*, 1999, 151:17–23.
Bettuzzi et al., Identification of an androgen–repressed mRNA in rat ventral prostate as coding for sulphated glycoprotein 2 by cDNA cloning and sequence analysis, *Biochem. J.*, 1989, 257:293–296.
Buttyan et al., Induction of the TRPM–2 gene in cells undergoing programmed death, *Mol. Cell. Biol..*, 1989, 9:3473–3481.
Choi et al., A serum protein SP40,40 modulates the formation of membrane attack complex of complement on erythrocytes, *Mol. Immunol.*, 1989, 26:835–840.
Choi–Miura et al., Relationship between multifunctional protein "clusterin" and Alzheimer disease, *Neurobiol. Aging*, 1996, 17:717–722.
Connor et al., SGP–2 expression as a genetic marker of progressive cellular pathology in experimental hydronephrosis, *Kidney Int.*, 1991, 39:1098–1103.
de Silva et al., Apolipoprotein J: structure and tissue distribution, *Biochemistry*, 1990, 29:5380–5389.
de Silva et al., A 70–kDa apolipoprotein designated ApoJ is a marker for subclasses of human plasma high density lipoproteins, *J. Biol. Chem.*, 1990, 265:13240–13247.
de Silva et al., Purificatioin and characterization of apolipoprotein J, *J. Biol. Chem.*, 1990, 265:14292–14297.
James et al., Characterization of a human high density lipoprotein–associated protein, NA1/NA2. Identity with SP–40,40, an inhibitor of complement– mediated cytolysis, *Arterioscler. Thromb.*, 1991, 11:645–652.
Jenne et al., Clusterin (complement lysis inhibitor) forms a high density lipoprotein complex with apolipoprotein A–I in human plasma, *J. Biol. Chem.*, 1991, 266:11030–11036.
Jenne et al., Molecular structure and functional characterization of a human complement cytolysis inhibitor found in blood and seminal plasma: identity to sulfated glycoprotein 2, a constituent of rat testis fluid, *Proc. Natl. Acad. Sci. U. S. A.*, 1989, 86:7123–7127.
Kirszbaum et al., Molecular cloniing and characterization of the novel, human complement–associated protein, SP–40, 40: a link between the complement and reproductive systems, *Embo J.*, 1989, 8:711–718.
Koch–Brandt et al., Clusterin: a role in cell survival in the face of apoptosis?, *Prog. Mol. Subcell. Biol.*, 1996, 16:130–149.

(List continued on next page.)

Primary Examiner—Andrew Wang
Assistant Examiner—Karen A. Lacourciere
(74) *Attorney, Agent, or Firm*—Licata & Tyrell P.C.

(57) ABSTRACT

Antisense compounds, compositions and methods are provided for modulating the expression of clusterin. The compositions comprise antisense compounds, particularly antisense oligonucleotides, targeted to nucleic acids encoding clusterin. Methods of using these compounds for modulation of clusterin expression and for treatment of diseases associated with expression of clusterin are provided.

13 Claims, No Drawings

OTHER PUBLICATIONS

Meri et al., Complement regulation, *Vox. Sang.*, 1998, 74:291–302.

Miyake, et al., Testosterone–repressed Prostate Message–2 is an antiapoptotic gene involved in progression to androgen independence in prostate cancer, *Cancer Res.*, 2000, 60:170–76.

Miyake, et al., Acquisition of chemoresistant phenotype by overexpression of the anitapoptotic gene testosterone–repressed prostate message–2 in prostate cancer, *Cancer Res.*, 2000, 60:2547–2554.

Moulson et al., Clusterin (Apo J) regulates vascular smooth muscle cell differentiation in vitro, *J. Cell. Physiol.*, 1999, 180:355–364.

Murphy et al., SP–40,40 is an inhibitor of C5b–6–initiated haemolysis, *Int. Immunol.*, 1989, 1:551–554.

O'Bryan et al., Human seminal clusterin (SP–40,40). Isolation and characterization, *J. Clin. Invest.*, 1990, 85:1477–1486.

Sensibar et al., Prevention of cell death induced by tumor necrosis factor alpha in LNCaP cells by overexpression of sulfated glycoprotein–2 (clusterin), *Cancer Res.*, 1995, 55:2431–2437.

Silkensen et al., The role of clusterin in tissue injury, *Biochem. Cell. Biol.*, 1994, 72:483–488.

Tschopp et al., Clusterin: modulation of complement function, *Clin. Exp. Immunol.*, 1994, 97 Suppl 2:11–14.

Urbich et al., Laminar shear stress upregulates the complement–inhibitory protein clusterin : A novel potent defense mechanism against complement–induced endothelial cell activation [In Process Citation], *Circulation*1, 2000, 101:352–355.

Yang et al., Isolation of Ku70–binding proteins (KUBS), *Nucleic Acids Res.*, 1999, 27:2165–2174.

\* cited by examiner

SEQUENCE LISTING

<160> NUMBER OF SEQ ID NOS: 90

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                    20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                    20

<210> SEQ ID NO 3
<211> LENGTH: 1648
<212> TYPE: DNA
<213> ORGANISM: Homo sapiens
<220> FEATURE:
<221> NAME/KEY: CDS
<222> LOCATION: (53)...(1402)

<400> SEQUENCE: 3

-continued

```
cgcggacagg gtgccgctga ccgaggcgtg caaagactcc agaattggag g c atg atg      58
                                                          Met Met
                                                            1 aag act ctg ctg ctg ttt gtg ggg ctg ctg c tg acc tgg gag agt ggg       106
Lys Thr Leu Leu Leu Phe Val Gly Leu Leu L eu Thr Trp Glu Ser Gly
      5                   10                    15 cag gtc ctg ggg gac cag acg gtc tca gac a at gag ctc cag gaa atg      154
Gln Val Leu Gly Asp Gln Thr Val Ser Asp A sn Glu Leu Gln Glu Met
 20                      25                     30 tcc aat cag gga agt aag tac gtc aat aag g aa att caa aat gct gtc      202
Ser Asn Gln Gly Ser Lys Tyr Val Asn Lys G lu Ile Gln Asn Ala Val
 35                  40                     45                 50 aac ggg gtg aaa cag ata aag act ctc ata g aa aaa aca aac gaa gag      250
Asn Gly Val Lys Gln Ile Lys Thr Leu Ile G lu Lys Thr Asn Glu Glu
             55                  60                     65 cgc aag aca ctg ctc agc aac cta gaa gaa g cc aag aag aag aaa gag      298
Arg Lys Thr Leu Leu Ser Asn Leu Glu Glu A la Lys Lys Lys Lys Glu
             70                  75                     80 gat gcc cta aat gag acc agg gaa tca gag a ca aag ctg aag gag ctc      346
Asp Ala Leu Asn Glu Thr Arg Glu Ser Glu T hr Lys Leu Lys Glu Leu
         85                  90                     95 cca gga gtg tgc aat gag acc atg atg gcc c tc tgg gaa gag tgt aag      394
Pro Gly Val Cys Asn Glu Thr Met Met Ala L eu Trp Glu Glu Cys Lys
    100                 105                    110 ccc tgc ctg aaa cag acc tgc atg aag ttc t ac gca cgc gtc tgc aga      442
Pro Cys Leu Lys Gln Thr Cys Met Lys Phe T yr Ala Arg Val Cys Arg
115                 120                    125                 130 agt ggc tca ggc ctg gtt ggc cgc cag ctt g ag gag ttc ctg aac cag      490
Ser Gly Ser Gly Leu Val Gly Arg Gln Leu G lu Glu Phe Leu Asn Gln
                135                    140                145 agc tcg ccc ttc tac ttc tgg atg aat ggt g ac cgc atc gac tcc ctg      538
Ser Ser Pro Phe Tyr Phe Trp Met Asn Gly A sp Arg Ile Asp Ser Leu
            150                    155                160 ctg gag aac gac cgg cag cag acg cac atg c tg gat gtc atg cag gac      586
Leu Glu Asn Asp Arg Gln Gln Thr His Met L eu Asp Val Met Gln Asp
        165                    170                175 cac ttc agc cgc gcg tcc agc atc ata gac g ag ctc ttc cag gac agg      634
His Phe Ser Arg Ala Ser Ser Ile Ile Asp G lu Leu Phe Gln Asp Arg
    180                    185                190 ttc ttc acc cgg gag ccc cag gat acc tac c ac tac ctg ccc ttc agc      682
Phe Phe Thr Arg Glu Pro Gln Asp Thr Tyr H is Tyr Leu Pro Phe Ser
195                    200                205                 210 ctg ccc cac cgg agg cct cac ttc ttc ttt c cc aag tcc cgc atc gtc      730
Leu Pro His Arg Arg Pro His Phe Phe Phe P ro Lys Ser Arg Ile Val
                   215                    220                225 cgc agc ttg atg ccc ttc tct ccg tac gag c cc ctg aac ttc cac gcc      778
Arg Ser Leu Met Pro Phe Ser Pro Tyr Glu P ro Leu Asn Phe His Ala
               230                    235                240 atg ttc cag ccc ttc ctt gag atg ata cac g ag gct cag cag gcc atg      826
Met Phe Gln Pro Phe Leu Glu Met Ile His G lu Ala Gln Gln Ala Met
           245                    250                255 gac atc cac ttc cac agc ccg gcc ttc cag c ac ccg cca aca gaa ttc      874
Asp Ile His Phe His Ser Pro Ala Phe Gln H is Pro Pro Thr Glu Phe
       260                    265                 270 ata cga gaa ggc gac gat gac cgg act gtg t gc cgg gag atc cgc cac      922
Ile Arg Glu Gly Asp Asp Asp Arg Thr Val C ys Arg Glu Ile Arg His
275                    280                285                 290 aac tcc acg ggc tgc ctg cgg atg aag gac c ag tgt gac aag tgc cgg      970
Asn Ser Thr Gly Cys Leu Arg Met Lys Asp G ln Cys Asp Lys Cys Arg
```

|  |  |  |  |  |  |  |  |  | 295 |  |  |  | 300 |  |  |  |  | 305 |  |  |
|---|---|---|---|---|---|---|---|---|---|---|---|---|---|---|---|---|---|---|---|---|
| gag | atc | ttg | tct | gtg | gac | tgt | tcc | acc | aac | a | ac | ccc | tcc | cag | gct | aag | | | | 1018 |
| Glu | Ile | Leu | Ser | Val | Asp | Cys | Ser | Thr | Asn | A | sn | Pro | Ser | Gln | Ala | Lys | | | | |
| | | | 310 | | | | | 315 | | | | | | 320 | | | | | | |

| ctg | cgg | cgg | gag | ctc | gac | gaa | tcc | ctc | cag | g | tc | gct | gag | agg | ttg | acc | 1066 |
|---|---|---|---|---|---|---|---|---|---|---|---|---|---|---|---|---|---|
| Leu | Arg | Arg | Glu | Leu | Asp | Glu | Ser | Leu | Gln | V | al | Ala | Glu | Arg | Leu | Thr | |
| | | 325 | | | | | 330 | | | | | | 335 | | | | |

| agg | aaa | tac | aac | gag | ctg | cta | aag | tcc | tac | c | ag | tgg | aag | atg | ctc | aac | 1114 |
|---|---|---|---|---|---|---|---|---|---|---|---|---|---|---|---|---|---|
| Arg | Lys | Tyr | Asn | Glu | Leu | Leu | Lys | Ser | Tyr | G | ln | Trp | Lys | Met | Leu | Asn | |
| 340 | | | | | 345 | | | | | | | | 350 | | | | |

| acc | tcc | tcc | ttg | ctg | gag | cag | ctg | aac | gag | c | ag | ttt | aac | tgg | gtg | tcc | 1162 |
|---|---|---|---|---|---|---|---|---|---|---|---|---|---|---|---|---|---|
| Thr | Ser | Ser | Leu | Leu | Glu | Gln | Leu | Asn | Glu | G | ln | Phe | Asn | Trp | Val | Ser | |
| 355 | | | | 360 | | | | | 365 | | | | | | 370 | | |

| cgg | ctg | gca | aac | ctc | acg | caa | ggc | gaa | gac | c | ag | tac | tat | ctg | cgg | gtc | 1210 |
|---|---|---|---|---|---|---|---|---|---|---|---|---|---|---|---|---|---|
| Arg | Leu | Ala | Asn | Leu | Thr | Gln | Gly | Glu | Asp | G | ln | Tyr | Tyr | Leu | Arg | Val | |
| | | | 375 | | | | | 380 | | | | | | 385 | | | |

| acc | acg | gtg | gct | tcc | cac | act | tct | gac | tcg | g | ac | gtt | cct | tcc | ggt | gtc | 1258 |
|---|---|---|---|---|---|---|---|---|---|---|---|---|---|---|---|---|---|
| Thr | Thr | Val | Ala | Ser | His | Thr | Ser | Asp | Ser | A | sp | Val | Pro | Ser | Gly | Val | |
| | | 390 | | | | | 395 | | | | | | 400 | | | | |

| act | gag | gtg | gtc | gtg | aag | ctc | ttt | gac | tct | g | at | ccc | atc | act | gtg | acg | 1306 |
|---|---|---|---|---|---|---|---|---|---|---|---|---|---|---|---|---|---|
| Thr | Glu | Val | Val | Val | Lys | Leu | Phe | Asp | Ser | A | sp | Pro | Ile | Thr | Val | Thr | |
| | | 405 | | | | | 410 | | | | | | 415 | | | | |

| gtc | cct | gta | gaa | gtc | tcc | agg | aag | aac | cct | a | aa | ttt | atg | gag | acc | gtg | 1354 |
|---|---|---|---|---|---|---|---|---|---|---|---|---|---|---|---|---|---|
| Val | Pro | Val | Glu | Val | Ser | Arg | Lys | Asn | Pro | L | ys | Phe | Met | Glu | Thr | Val | |
| 420 | | | | | 425 | | | | | | | | 430 | | | | |

| gcg | gag | aaa | gcg | ctg | cag | gaa | tac | cgc | aaa | a | ag | cac | cgg | gag | gag | tga | 1402 |
|---|---|---|---|---|---|---|---|---|---|---|---|---|---|---|---|---|---|
| Ala | Glu | Lys | Ala | Leu | Gln | Glu | Tyr | Arg | Lys | L | ys | His | Arg | Glu | Glu | | |
| 435 | | | | 440 | | | | | 445 | | | | | | | | |

| gatgtggatg | ttgcttttgc | accttacggg | ggcatcttga | gtccagctcc | c cccaagatg | 1462 |
|---|---|---|---|---|---|---|
| agctgcagcc | cccagagag | agctctgcac | gtcaccaagt | aaccaggccc | c agcctccag | 1522 |
| gcccccaact | ccgccagcc | tctccccgct | ctggatcctg | cactctaaca | c tcgactctg | 1582 |
| ctgctcatgg | gaagaacaga | attgctcctg | catgcaacta | attcaataaa | a ctgtcttgt | 1642 |
| gagctg | | | | | | 1648 |

<210> SEQ ID NO 4
<211> LENGTH: 18
<212> TYPE: DNA
<213> ORGANISM: Artificial Sequence
<220> FEATURE:
<223> OTHER INFORMATION: PCR Primer

<400> SEQUENCE: 4
tccgtacgag cccctgaa                                                     18

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
tgagcctcgt gtatcatctc aag                                               23

<210> SEQ ID NO 6
<211> LENGTH: 21
<212> TYPE: DNA
<213> ORGANISM: Artificial Sequence
<220> FEATURE:
<223> OTHER INFORMATION: PCR Probe -continued

<400> SEQUENCE: 6
tccacgccat gttccagccc t                                              21

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
caacggattt ggtcgtattg g                                              21

<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
ggcaacaata tccactttac cagagt                                         26

<210> SEQ ID NO 9
<211> LENGTH: 21
<212> TYPE: DNA
<213> ORGANISM: Artificial Sequence
<220> FEATURE:
<223> OTHER INFORMATION: PCR Probe

<400> SEQUENCE: 9
cgcctggtca ccagggctgc t                                              21

<210> SEQ ID NO 10
<211> LENGTH: 8133
<212> TYPE: DNA
<213> ORGANISM: Homo sapiens

<400> SEQUENCE: 10
gccatgttgc ccaggctggt ctcaaactcc taagctcaag taatcctcct a ccttggcct    60 cccaaattgt tgggattata gatgtgtgcc actatgccca gccaatgtaa g attttgtag   120 tatattagtg ttgctcctgt cctctgctgc agggcttttt tgattgggac t cagtgaatt   180 gctccaatcc ctgaagtcac atcagttggc ccttagccga gcgggggtgg a tatcattgg   240 tggccaaaga tgacagtgaa tgaacctgaa atgttgggcc ttgtgacttt t gggcctcca   300 ggtgtctcaa aactgtcccc catggaggga gataaaagga aagagcatgg a cctgacaga   360 tggggtgctg ggggctggtc ccagctgggc tgttggtcac ttgctgtgtg a ctgttacag   420 ccatgggcag ggcctggcct ggctcaccag ggggtgggag gccaggaggc c gtggccttg   480 gtgagcttct cctaactgtg cccatgctgg ctgtcccagc ttgaggagtt c ctgaaccag   540 agctcgccct tctacttctg gatgaatggt gaccgcatcg actccctgct g gagaacgac   600 cggcagcaga cgcacatgct ggatgtcatg caggaccact tcagccgcgc g tccagcatc   660 atagacgagc tcttccagga caggttcttc acccgggagc ccaggatac c taccactac   720 ctgcccttca gcctgcccca ccggaggcct cacttcttct ttcccaagtc c gcatcgtc   780 cgcagcttga tgcccttctc tccgtacgag ccctgaact tccacgccat g ttccagccc   840 ttccttgaga tgatacacga ggctcagcag gccatggaca tccacttcca c agcccggcc   900

```
ttccagcacc cgccaacaga attcatacga ggtgagaagg ggtggaagct c atggccttt      960
tgagcaactc gttagatgct gagaaccatg ccgagggctc agcgggtgtc a tctcgattt     1020
ttctccagca atatcacaag ggtgatatta tccttattta aagaggaaaa a aactgagct     1080
gggcatggtg gctcatgcct gtgatgccag cactttgaga ggccaaggcg g gaggatcat     1140
ttgaggccag gagtttgaga ccagcctggc caagatagtg agaccctgtc t ctacaaaaa     1200
taaaaactta aaaaattagc cgggtgtggt ggtgcacacc tgtagtctca g ctactcggg     1260
aggctgaggc aagagagtca cctgagcctg gaagttggag gctgcagtga g ctatgattg     1320
caccattgca ttccagcctg gcaacagag tgagaccctg tctctaaatt a aaaaataaa      1380
taaaaataac aataggaatc agtggagtcc atctctgcat ggctggatga c tgactcttc     1440
ttccctcgtg tgtccccaga aggcgacgat gaccggactg tgtgccggga g atccgccac     1500
aactccacgg gctgcctgcg gatgaaggac cagtgtgaca agtgccggga g atcttgtct     1560
gtgggtgagt cggggtccag accacaagcc gtccccctg atcccttgtg t cctggggtc      1620
actgggcct cactggtgct gcctttatgg agtcagacag ataagcgttt g gattccagc      1680
tctgcagcct ttgagctgtg tcccggggca ggtcctgagc ctcatgcagc t tcggttcct    1740
catcttagaa tgagatgatg atgcgaggct gtccctgaag tcggtgagat g tcgttagag    1800
atgcaaaagt gccctccacc tggtcggccc catgttgaaa aaagcttgtt g aaaaaagtc    1860
atcccctgg gactccccgg tgattctgtt cccaagcgcc aagcagtagg c atcttcatt    1920
ttcctctgca gattatgaca ttgcagacag tatgtgtttt gtttaacaaa a ctgaccaga    1980
ggccaggcac tgttctaaac actcgacata catttcctca tttcctcaga a tgaccctct    2040
gaggaaactg agccacagaa aggttaataa cttatccaag attgacccccg a catgggcga   2100
gctgggcttc aatcctaggg cgctgtgttc tctcctgggg cccctcgcag c ctctgccac    2160
agaagtcacg ggtctcagta cctgggcatc caagcaatag tcccttttggt c ggttggttg   2220
gtcccctagg caaagggaat atttcccttt aactgtcccc ctccgtttca c cagctctgg    2280
ttatggggta acttcctttcc acttagagat aacagctgtg acagtatttg g actagttcc   2340
tggtacacag cagttcatac tcacaaagag ttaattgttt ccccttgttc a acagcttat   2400
cgatctggtg gctttgctct tacttaatgc ttagtttgag tttgccatgg c aggccgcca   2460
gggtctagtt aaacattcct agcctcactc ctataatttt agaagccact g caaaataaa    2520
cagttgtgct ttaacaggct gaagtataag ttgctgtaga tgagtgcaca a ccaggcctt   2580
ggggcttttt ctataaaaaa tatcatagag tggcatcaat tacatggtac c tcaccacaa   2640
gaaagtcatg ttagggtctg agaaaagatg tcagatgcct gtgcccagat t ggacctctt    2700
atagctgatt tttactctgt tgcccaggct gggtcaggtc tggcccaatc t taacagtca    2760
ttgattacag ttgagagtgc agccagcgcc agtcttatca gtcattgatt a tagctggcg   2820
tacagtggct ctatctcggc tcactgcgac ctccgcctcc tgggttcaag t gattctcct    2880
gcctcagcct cccaagtagc tgggagtgca ggtgtgcacc accacaccca g ctaattttt    2940
gtatttttag tagagacagc atttcactat gttggccagg ctggtcttga a ctcctgacc   3000
tcaagtaatc tccccgcctc ggcctcccaa agttctggga ttacaggtgt g agccactgt    3060
gcctgacctg agatagattc ttagagaatt attggtaaga ataattctct a agctgagct    3120
aaatagtcta cactgaagag gactgcctac tgttatttaa ggtgcttgca a ccatataag    3180
catgtactgc ctgggaactc tagatgagga tttctcaatt tcagcgctgt t gatttttt    3240
tttttttttt gagacagggt ctctctctat cacccagcct ggagtgcagt g gcaccatta   3300
```

```
cagctcactg cagcctagac ctcttgggct gaagtcatcc tcctgcctca g cctcctgag     3360 taacagacta caggtgtgct ccaccatgct tggctaattt ttttatttttt a gtagagatg    3420 gggtcttgct acattgccca agctggtctc taactcctgg gctcaagtga t cctcctacc    3480 tcagcctccc agagtgctgg gattacaggt gtgagcagtg ctgacatttt g gaccaggtc    3540 attctttgtc gttgggggct gtcctgagca gttcaggtt tttggcagca t tcctggcct    3600 ctgcccacta gaggtcagca gctcccttcc ctttgttgtg acaaccagct t cagaacttg    3660 ctaaatctcc ctgggtgaca gcgtccacag tagagaacct ctattctaga c taagcctca    3720 gctcttaagg attttctta ttttattatt attttttaa gacagggtct c gctctatca    3780 cccaggctgg agcgtagtgg cgcaatcttt gctcactgca acctctgctt c ctgggttca    3840 agcgatttct cctgcccag cctcctgagt agctgggatt acaggcgtgc a ccgccacgc    3900 ctggctaatt tttatatttt tagtagagac agggtttcac catattggcc a ggctggtct    3960 caaactcttg acctcaagtg atcagcctgc ctcagcctcc caaagtgctg g gattacagg    4020 tgtgagccag cacgcctggc tagttttct tattttaaa ttttttttg g taaaataat    4080 gatgtttatt tattacatat ttattttcaa actggcatct tgttagtaat t ctgtttctt    4140 tccccaccta acattttgtt tactataaat gatttcagtc atcatcctaa a gcatatgca    4200 aaatctccct tcccctgact cacgtttgat gtacctgcct ctggatattt t tgaaatacc    4260 ttaggggag aaaacagta gttttaagag ctagtggaca gtttccaggt c ttaatgaat    4320 ctgacaacct gcagcccagg gccaagagga atgaattctc ttttccctgc t ctcttgatg    4380 aactcactga ccagccatgg gcggcaggtg ggcaggcaag gacccctggc c accaggtgc    4440 cagtgcatca gctgcatgaa ctcctggcac cagaactgcc acctctacag a catgctcaa    4500 aagacaagtt tggaccgggt gcattggctc acacctgtaa tcccagcacc t tgagaggcc    4560 gaggtgggtg gaccectgag gtcaggagtt tgagaccagc ctagccaaca t ggtgaaacc    4620 ctgtctctcc taaaaataca aaaaaatcac ccggggtgg tggcaggcac c tgtaatccc    4680 aactactctg gaggctgagg caggagaatt gcttgaaccc gggaggtgga g gttgcagtg    4740 agctgagctc gcgccattgc actccagcct gggaaacaag agcgaaattc t gtctcaaaa    4800 aaaagacaag cttggaggat tgtccagaac cacagatcca gggtaggaaa a gcccaagct    4860 taggagctga agaccctggt tcaatcccgg gcccagagat catttattct a tggctttag    4920 gtaagctatt tattgatact tctgtgggcc tcagtttcat tattggtaaa a attatttca    4980 ttattggtaa aattaggact taagtcctaa tccttaagtc agaacagatc c aattcttag    5040 agaaaaagga tatccagaga gaactttctg cggtgtctgg gacgcaggca g tgccacacg    5100 aatggcagct gtgagtaata ttcctcctct ctggaaatga ttcccgggag g actagggca    5160 acgagagcca ctccaggtct gagaacatgg agaacttgag atcagtgctt t ggaagtgt    5220 ggtcaacaca gtttgtcacc aaagagataa gggtctggca cccaaagata a atgaatgat    5280 gttacgaagc acactgttta ggtcagttgg cgtatttttc cagagcaagg c ttctcaggc    5340 tgggcgtggt ggctcacacc agtaatccca gcacttttg ggcagatggg t tgagcccag    5400 gagttcgaga ccagcctgga caacacagag aaacccgtgt ctacaaaaa a tacaaaaat    5460 tagctgggca tggtagcatg tgcctatagt cccagctact caggaggctg a ggttggagg    5520 acagcctgag cctgggaagt caaggctgca gtgagccgag atctcaccac t gtattccag    5580 cctaggcaac agagcaaaac tctgtctcaa aaaacaaaa acaaaaacaa a aacccaaa     5640
```

-continued

| | | | | |
|---|---|---|---|---|
| agactttctg | gatgacggaa | gcagtgtcta | gattcacatt | ctgaggcaaa a cctttattt | 5700 |
| tgtcgtggac | aattccagtt | tgtggccctt | ccettaggga | agcactgctt t tgttcccgc | 5760 |
| tgcatgtgct | aacttccatt | cattcatggt | tctatccctt | tgtagccttc c cttcacact | 5820 |
| tctcacttgc | gtttcttcca | tctctgggca | gactgttcca | ccaacaaccc c tcccaggct | 5880 |
| aagctgcggg | gggagctcga | cgaatccctc | caggtcgctg | agaggttgac c aggaaatac | 5940 |
| aacgagctgc | taaagtccta | ccagtggaag | atgctcaaca | cctcctcctt g ctggagcag | 6000 |
| ctgaacgagc | agtttaactg | ggtgtcccgg | ctggcaaacc | tcacgcaagg c gaagaccag | 6060 |
| tactatctgc | gggtcaccac | ggtgagctgt | gtcccggcca | catgctgtgg c tcgggagcc | 6120 |
| gagctgtgat | cggagcaggg | ggcatgtgtg | cttttgactg | agcatttatc a cacggcaga | 6180 |
| aaatagaaaa | ctttaggcgc | ccctgttgcc | ttgaagcctc | atcacccact c agggaaaat | 6240 |
| ataaccctgc | tttacaaagg | agcaaagtaa | gagaggttcc | acagcttggc c aaggtgtga | 6300 |
| tagctgacag | atgacttgga | cgggtatttg | aacctgactg | cctggctgcc a agcctgtat | 6360 |
| tttgttgttg | ttgttttttgt | tttggtgcac | aaatctgtga | ataaaccaga a gcctctgtt | 6420 |
| cttttctcaa | agctacaagg | ctgccctctg | gcatgtaaaa | tggcttatga a ttagtacat | 6480 |
| cactctctgc | cagtgataaa | aacttctctc | taggccagac | atggtggctc a tgcctgtaa | 6540 |
| tcccagcact | ttgggaggca | gaggcaagag | gattgcttga | ggccaggaat t tgagaccag | 6600 |
| cctgggcaac | acagcaagat | tccctctcta | caaaaaatac | aaaaatcagt c aggtgtggt | 6660 |
| ggcacacact | tgtagtccca | gctattcagg | aggctgaggt | gggaggattg c ctgagccct | 6720 |
| gaagtggagg | ctgcagtgag | ctgtgatcac | gccactgcac | tccagcctgg g tgacagagt | 6780 |
| gagactctgt | ctcttaaaaa | atatatatat | ataaaataat | aaaataaagt t aaaaaatca | 6840 |
| aataaaactt | atttctagta | ctgggaactc | ttcttttttct | tttctttcttt c cctccaggc | 6900 |
| cctctggatt | ccttttctac | cctactctga | ccaagggctg | cctaaagcaa a tgtttggaa | 6960 |
| accacttttta | ttcttttgggg | tgctccctgg | ctggtcattt | gcagatgaca t ttgccccaa | 7020 |
| cacatgagtg | tctgtgaacc | aggtccgttc | tgtccactga | gctgtactta c gtctagatg | 7080 |
| tataagaagc | atggggtcag | ctctctaggt | tccttggagg | agcaggagga c ttccttatc | 7140 |
| agaagcctga | cttctgttgc | agagcgcatg | cattttgacc | acagtgtttc a gctcttccc | 7200 |
| ttttctcttg | ttccatttag | gtggcttccc | acacttctga | ctcggacgtt c cttccggtg | 7260 |
| tcactgaggt | ggtcgtgaag | ctctttgact | ctgatcccat | cactgtgacg g tccctgtag | 7320 |
| aagtctccag | gaagaaccct | aaatttatgg | agaccgtggc | ggagaaagcg c tgcaggaat | 7380 |
| accgcaaaaa | gcaccggtaa | gcaggcgggc | ctttcctgcg | gcctgcaggg c ccagtgagt | 7440 |
| ctctgggagc | cacaaaaaaa | caaacaaagt | gcagactcta | tagcctggtg g gaacgactc | 7500 |
| cgcccggagc | cagagcccaa | gaacaaagcc | aggaagttac | gggggaattt t attttttcct | 7560 |
| ttggaggatg | ttttactttg | gaggataact | gttttttatt | tcaggaggag t gagatgtg | 7620 |
| gatgttgctt | ttgcacctac | gggggcatct | gagtccagct | ccccccaaga t gagctgcag | 7680 |
| ccccccagag | agagctctgc | acgtcaccaa | gtaaaccagg | ccccagcctc c aggcccca | 7740 |
| actccgccca | gcctctcccc | gctctggatc | ctgcactcta | acactcgact c tgctgctca | 7800 |
| tgggaagaac | agaattgctc | ctgcatgcaa | ctaattcaat | aaaactgtct t gtgagctga | 7860 |
| tcgcttggag | ggtcctctttt | ttatgttgag | ttgctgcttc | ccggcatgcc t tcattttgc | 7920 |
| tatgggggc | aggcagggg | gatggaaaat | aagtagaaac | aaaaaagcag t ggctaagat | 7980 |
| ggtatagga | ctgtcatacc | agtgaagaat | aaagggtga | agaataaaag g gatatgatg | 8040 |

```
acaaggttga tccacttcaa gaattgcttg ctttcaggaa gagagatgtg t ttcaacaag    8100 ccaactaaaa tatattgctg caaatggaag ctt                                  8133
```

<210> SEQ ID NO 11
<211> LENGTH: 940
<212> TYPE: DNA
<213> ORGANISM: Homo sapiens

<400> SEQUENCE: 11

```
aagcttgaac tggagcaagg gtaggcactt gcatgctggg tggccagcct a tgggaaggc     60 tcgccctggg gcagagggcc tggcacccag cagctctttg agtgcatgag c ctgtggtct    120 ctgtgtgctc agccagcctt tgtgtcttcct gtaggatgcc ctaaatgaga c cagggaatc   180 agagacaaag ctgaaggagc tcccaggagt gtgcaatgag accatgatgg c cctctggga    240 agagtgtaag ccctgcctga aacagacctg catgaagttc tacgcacgcg t ctgcagaag    300 tggctcaggc ctggttggcc gccaggtgaa aaggggacac atgagtggcc a aggctctga    360 gtggggaagg aggggagcct agtgaaatat gcttcattcc gcatgccaga t gcaattgat    420 tagcattggc tggcttgccc agagtgccat gctccattgg taatgtctgg c atgagtaga    480 gagagtggag tcatcaaaag gatgtaggcc aggtatctgc cttctcttag a aaactcatg    540 cagcagtgct tagctggatg acataataaa ctgcttcgtg ggatgcagag c cctgtgtca    600 cttatgtgga aggatttaag aatttttttt ttttttttgag acagggtctc a ctctgtcac    660 ccaggctgga gtacagtgat gtgatcatgt ttcactgcag cttcgacctc c tgggttcag    720 gtgatcctcc cacctcagcc tcccaagtag ctgggactac aggcacgtac c accacaccc    780 agctaatttt tgtattttt ttttgtaaac atggggtttg gccatgttgc c caggctggt    840 ctcaaactcc taagctcaag taatcctcct accttggcct cccaaattgt t gggattata    900 gatgtgtgcc actagtccca gccaatgtaa gattttgtag                           940
```

<210> SEQ ID NO 12
<211> LENGTH: 7610
<212> TYPE: DNA
<213> ORGANISM: Homo sapiens
<220> FEATURE:
<221> NAME/KEY: unsure
<222> LOCATION: 5461
<223> OTHER INFORMATION: unknown
<221> NAME/KEY: unsure
<222> LOCATION: 5462
<223> OTHER INFORMATION: unknown

<400> SEQUENCE: 12

```
gacctgcagg tcaacggatc cattcccgat tcctcatcgt ccagatggaa g aaactgagg     60 cccaagggca aagtgattag tccgaggtca cccagtgtct aggggcacac c taggactgt    120 aatcagactt tcatggacct ggtctggtt ctcccactta gtcatgggcc t gaagattc    180 cccgaggctg cctcctgaaa aggactgggg tctagtggcc cctggacgtt g gcaagcaa    240 gggactgggc ctccatgttg tgcctccata gtcctgatcc tgaactggaa a actcagccc    300 ctgaccacgc agctctcctt taagccccctt tgtttcacat ggttttcaaa g tctgccacc    360 cacagtgggg ctgcctgtac ccgccctgtc cacccattgc cccagctgtc a gcccttga    420 cttctctcct ggggcttaaa catccctggc tccaaaatgg gcagctcact t tcttcccca    480 agaagtagct gcacctccag ggttcctaga tttgccccctc cttgccaggg g gaggggtgg    540 ctgcgacagg agattctccc tgctctcagc agaaggaact ccagcagttg g agaccagca    600
```

-continued

```
aacccctctg gacacagatc tgatttccta actgggaagg ctcagggcaa a ataaaaatt    660 caggtccact ggttcaaaaa ctatgaagaa tttcaagacc gtcacagtag c ccattaaac    720 caaacgtgga tctgcaaggg tcccacagcc atgaagccca ccctgcttgg t tgggttcca    780 aaaagatggg gacagtgatt gcttaagctc tgtggatcaa ggaccccgga g aggccttct    840 ggctctccac atatctgctc tgatcactcc taaacacaat tctgtttcct c caggcctgg    900 cgggtcagtc cagggacccc catcagtgtg atgtttccag gagtaggcgt t tcaatactt    960 cctgtgctct cttctccagc acaaggcccc tctccatccc accctcatta t gtctgactc   1020 tttactattt aaatgggtca agagaagtgg cgcttgtgta atgtgaaggt t aaggtcagt   1080 agggccaggg aactgtgaga ttgtgtcttg gactgggaca gacagccggg c taaccgcgt   1140 gagagggctc ccagatggca cgcgagttca ggctcttccc tactggaagc g ccagcgccg   1200 cacctcaggg tctctcctgg agccagcaca gctattcgtg gtgatgatgc g cccccccgc   1260 gccccagccc ggtgctgcac cggcccccac ctcccggctt ccagaaagct c ccttgctt   1320 tccgcggcat tctttgggcg tgagtcatgc aggtttgcag ccagcccaa a ggtgtgtgc   1380 gcgaacggag cgctataaat acggcgcctc ccagtgccca caacgcggcg t cgccaggag   1440 cagcagcatg ggcacagggt ccgtgaccgg tgagatgtcc ccgtcttccc t acccttgag   1500 cagagccaca ccaggacgga tgggcgggca ggggatggca gccaggcaga g agggatgac   1560 acagctcgca gtcacaaccc ctgcgctttc gacggagccc aggaagccag g gaggggagg   1620 tgccggagcc ccatcaccag gcagctgagc caggggccgc gcaaccgccg c ctgatgagc   1680 acgagcttca cgcaaccaca attctgtggt gggggggtaa atagaacaga t ataatgatc   1740 atcctttcgc aaagatgggg aaactgagac ctggagacct gccgcgttgg c agacccagg   1800 ctagcaggtg acagagctgg cctgcaccga gctccttcct gcagcatatc c tctgcgaag   1860 atgcggatct ctcagttgtg gctttcggct tgcatgcatg agtcatctag t tttcttcta   1920 aattctctag ctctctggac actgttgcct gtaagtatga ggctgcggat t tcagtatat   1980 ctgcaaccac cgaaatccga cttttttctgc ctcctaatgc atctgaggtg c atcagagaa   2040 aagtcacaca agatccacca ggcctcgagac ctctgattcc acagtctcat t ttacagatg   2100 ataatctgag gcctggagag gtttaggact ggtgccaaca ctaaacagca a ataagtatc   2160 agaattggga ttcgagccaa agcctcttga ccttccagaa tttctggacc t agttaaaaa   2220 aaatatgatt tttattatta tttttaaac ggagaggtta ggaatttaaa g gaaagtaca   2280 gatactatat aaaaaaagat gcccatgaaa atgttaagtt ataataatag t ggagcattg   2340 ggcacaactg aaatggccaa tcttgtgaga atggtaaaat aaacttaggt c cgtgagtaa   2400 gtggagtatt acatagccat aaaagtatgc ccttaaagaa tatttgaaga t ggtgaatgt   2460 gaagaatctt gtataaactg catggaagac agaaggaaat ataccacagt g ctaacctttt   2520 gcctctgggt gatatgaatt accggtgatt attttttctta ttttccttttt g gtttagttt   2580 tctccatttg aagaagcaga taggagccgg ggctttggga ttgaaccct c accatctgt   2640 gtgccctctt cactgtcttc ccatcctccc cacggctccc tgttcacagt c attgatttt   2700 cttctttct tttctctttt ttttttttt tcctgagacc aagtctcact c tgttgccca   2760 ggctggagta gagtagcgcc atctcggctc actgcaacct ccgccatccg g ttcaagca   2820 gttctcatgc ctcagcctct gagtagctgg gactacagcc gcatgctgct a catccggct   2880 aatttttgta ttttagtag agacatggtt tcaccacctt ggccaggctg g tctcgaact   2940
```

-continued

```
cctgatctca agtaatccag cctgtcttgg cctcccaaag tgctgggtg a caggtgtga    3000 atcaatgcgt ccctgccagg tcattgattt tcttaagcct ctagccctgc c ctgcttgga   3060 aacgttttgg gaagctgctc agttcaaagt tcccaggagt gtgtgcctgg a gggagttg    3120 ctcccaaagt ctgcctgctc ccccgcccc cctgcccc caccccccgc c atcttctcc     3180 tcctcctctt ccctgagca gccctttgt ccacagaacc ggccttttct g gtagaagga   3240 gcaaggccaa gtggtttaag ccttcttagg gagaatgagg ctgtgtggta g tgctgggga  3300 ctcgagggcc ttgcgttggc atggctcttc cacccagggc agctggcagc c aggctccca  3360 ggaggcagag gagatgaggg gggaggtgag tccgagcaaa ggaaaggagg t cggctgtgc  3420 agtcacggtt ctagaacatt cattggatca gcagcatcca tatcacctgc a gactggctg  3480 gaaaagcagt ctcagaacca acattataac cagccctgca gtgattcata a gtactttaa  3540 aaagtggtca atcatttcag caaagcagag ccacacagtc cggggaccca c aggtggcct  3600 ctgtgtgctt gtctcggttt tcctgcccct ctccagacat gttgattaga c actgccaat  3660 gcccagcctc agacctcagt ctaatttgga agtagtcaga atttactatg a ttacataag  3720 accctcgtgt ttacagaaca cattcccctc tctgaggtct ggattagatc c attttacag  3780 atgaagaaac tgaggctcag atatttaagt gacttggaat caaggaaaga a tactggaca  3840 tggggctggg agggctgggc tctcatccca gggttaccat gagcatgctg t ggactctag  3900 ggagtccatg ccctctctgg cgttcagctc accgctaggt agagaggttg g gtgagagaa  3960 cgacctcctt cccaggtctg agctggatgg ttcaccaggg accccaggct c cctggacga  4020 gactctgtgc ccgctgctga gtctggaatt cctttcctgt atcttgcctt t gcgtgcccc  4080 attcttcatg gcccagcacc ctgtcttctg gtcagaacct agttctgaat g gttttttcc  4140 agaagttgtt gctttcaggg gcccctggca gagaggtgtt tctggctggc t ttgtctctc  4200 tggcatgaca aaggctctgt tcctgctgga ggcatttcag ggctcagtgg g cagctgggg  4260 cagacgctga gaccacagcc ttcctggtga gcccggtctc cgcccctac c ccatctctg   4320 ggaaggcgct gaccccatct cttctcccac gctgctccct ggctctttgc g cctgattac  4380 ttctcatgag aggcactcct tgttaatgtg ctactgagtg tccagatggg c ctgctgggc  4440 tgagcgggct ttgatgtga accatttcag gaaggggaac ccatcgtcct g ttggttctg  4500 tgatggcaaa tgggtgagct cagataacga gttcttggga gggcatggt g ggggtggag   4560 tgcaggggga gggttttctg ttttattgac aacagcctca gcttctggga a aggtccat   4620 tgtgtaagac cggggctatg gctgtgcccc gtggctcagg gcagccagcc a gtggtggca  4680 ggaacactgg cagggcagcc tcgtgtcggc ttagagggga tgggcagtgt g gagggcctg  4740 gcagagcaag aggactcatc cttccaaagg gactttctct gggaagcctg c tcctcgggc  4800 cactgcgaac cctctctact ctccgaagga attgtccttc ctggcttcca c tacttccac  4860 ccctgaatgc acaggcagcc cggcccaagt ctcccactag gatgcagatg g attcggtgt  4920 gaagggctgc ctgctgttgc ctccgcgtct tgaaagtcaa gttcaggtgg t gctgagact  4980 ccctgggggc tgcagcgctg tggtgaatgg ggagcgtctg ctgggtgaa g gtttaggtg  5040 cacattgcag aggacgtggc tggtctctgg gatgcagtcc ctctgtggag g tggcatggg  5100 gagggacgga tgcatgacct aagggtggta ttttcagtgt ctgacatgat c gataccact  5160 ctggacaagg aggccaggat gcagaaagcc tgtgtgcctc gctgattgtc g gggaggatg  5220 tggcttggac aagagcctgg ttcctccgat gccaggttc ttgtttcttc c actcaacat   5280 tgctgtcctg cagtccctcc ctccctgcac ctcctgcctt cgctttcatt c gaggtgtcc  5340
```

```
atggcaagtc tggtcatttc cccccatttc ctcaggaata aaagttgcag c agtgcctgc    5400
tgtggggaca gctgagggca gtgaggctgg ggagctgctg cagggcggag t gggcgggac    5460
nnagcaggct gtctagctgt tcccatgatg gtctcctgtt ctctgcagag g cgtgcaaag    5520
actccagaat tggaggcatg atgaagactc tgctgctgtt tgtggggctg c tgctgacct    5580
gggagagtgg gcaggtcctg ggggaccaga cggtctcaga caatgagctc c agggtgagt    5640
agaccaagca tgatgttcct ctggccacag ggtgatgagg tcagagggca g ggtagctaa    5700
ttctgctcag tgcctctcta tcaggcccca gtgttacaga ccgtttttat c ttgtgcact    5760
gggtctgggt gcctgtgtct gggcccactc tgagcctcag ctcccaggcc c tggttcag    5820
gctctgcgtg catcagactg ccggcatttg caggcatttc ccaagcactt t cggctgttg    5880
catttcattc agctcttccc ctcccaggcc ccttagccca gctcccaggc c tcctccaca    5940
aagctgtgtc tggaccaccg gagctcttat ccctctcccc tttggagtgc c cagagctta    6000
tccctcctgt gagctgacgg tttctgcagg atcattgtta aaacccaga t cagacatgg    6060
gtgtgagtct gtttcacctc ttctcagctg ggtgactttg ggccactatc t tgatctcat    6120
gacactcccc ccaccccca ttttattgag atataattaa caaataaaaa t tgtgtatat    6180
ttaaggtata tgacgtgatg ttttgaaatg cacatacatt gaaatgatga c cagttttta    6240
tggtgggacg gtgggaagac ttaaaatcta cttcttagc aaatttccag t tatgatatg    6300
gtgttattaa ctataagcac cacctgtatg ttagacctcc agaacatact c ctcctacct    6360
gatgaacact ttgaccctt atcatatcac acttcccatg tctccctctg c gaagtgggc    6420
acggcggggg gctggagcat tacgtaaaact gcacatgaag tgtttggcgc a gtgcttggc    6480
atgggataaa caccagtgaa gtagcactta ggtgacacag tgtttcgctg c atttgtcac    6540
cagtgctatc cttactcatt tactcatctt cttattcctg tcgcctggca c tgcattgga    6600
acaaagaaat acacatatct gtttaaactg aactctagaa agatttgtgt c caaaataac    6660
aatattttat atttgatgc tgcaaacgtg acacttctgg gtttttttt t ttccttgcc    6720
aagtttcttc tgcacccagc tcattctcca ggggcacatg gcagtggctg g gcataactc    6780
tgggtgtgcc ggctcccatg gtctgcattt ctaagcagta gggtgcagtc a gcaaggagc    6840
ctgtgatggg agcctgtgcc agggcaaggc tgggcatgc tgctgcctgc t ggcaggagt    6900
gggggtccca gccttgacag cccctgaact gaacgggcct ttctggcatc c agctcattc    6960
cagggtcctg aggccacctc ttcctctcgc ctcattctgc ctcttgcact t tcttgcag    7020
aaatgtccaa tcagggaagt aagtacgtca ataaggaaat tcaaaatgct g tcaacgggg    7080
tgaaacagat aaagactctc atagaaaaaa caaacgaaga gcgcaagaca c tgctcagca    7140
acctagaaga agccaagaag aagaaagagg tcaggaggag ccgctaccgc c tccctgcct    7200
tgaccatccc actggagggg agggagggg tcactgcgcg gtgccctgct g gttgccatg    7260
gtgacccgca gtcctcccag gctgtgtcag ctgatgctga ggctgcagtt a agaagcagg    7320
gaaggttcat ttgcttctga aagcatcagg gagtgagatc ttggatctgg t tttgttatg    7380
agcctggccc agggctaatg ccagattcat ttcaatagat gtttctaagc c ctgatcacg    7440
tgctagttcc aagcaggctc tgggtggggt ggcggcaggg gccagacagg c gtggcgtcc    7500
aaccttcagg aagcttctag gagttaggga acagttggat cttgaaggat g agtgggttc    7560
tttaagccag gtgggaaggg gattccaggt gggcgaatga ggggaagctt               7610
```

<210> SEQ ID NO 13

-continued

```
<211> LENGTH: 1651
<212> TYPE: DNA
<213> ORGANISM: Homo sapiens
<220> FEATURE:
<221> NAME/KEY: CDS
<222> LOCATION: (199)...(1545)

<400> SEQUENCE: 13
ctgcgaaccc tctctactct ccgaagggaa ttgtccttcc tggcttccac t acttccacc      60 cctgaatgca caggcagccc ggcccaagtc tcccactagg gatgcagatg g attcggtgt     120 gaagggctgg ctgctgttgc ctccggctct tgaaagtcaa gttcagaggc g tgcaaagac    180 tccagaattg gaggcatg atg aag act ctg ctg ctg ttt  gtg ggg ctg ctg      231
                    Met Lys Thr Leu Leu Leu Phe Val Gly Leu Leu
                     1               5                  10 ctg acc tgg gag agt ggg cag gtc ctg ggg g ac cag acg gtc tca gac      279
Leu Thr Trp Glu Ser Gly Gln Val Leu Gly A sp Gln Thr Val Ser Asp
            15                  20                  25 aat gag ctc cag gaa atg tcc aat cag gga a gt aag tac gtc aat aag      327
Asn Glu Leu Gln Glu Met Ser Asn Gln Gly S er Lys Tyr Val Asn Lys
        30                  35                  40 gaa att caa aat gct gtc aac ggg gtg aaa c ag ata aag act ctc ata      375
Glu Ile Gln Asn Ala Val Asn Gly Val Lys G ln Ile Lys Thr Leu Ile
    45                  50                  55 gaa aaa aca aac gaa gag cgc aag aca ctg c tc agc aac cta gaa gaa      423
Glu Lys Thr Asn Glu Glu Arg Lys Thr Leu L eu Ser Asn Leu Glu Glu
60                  65                  70                  75 gcc aag aag aag aaa gag gat gcc cta aat g ag acc agg gaa tca gag      471
Ala Lys Lys Lys Lys Glu Asp Ala Leu Asn G lu Thr Arg Glu Ser Glu
                80                  85                  90 aca aag ctg aag gag ctc cca gga gtg tgc a at gag acc atg atg gcc     519
Thr Lys Leu Lys Glu Leu Pro Gly Val Cys A sn Glu Thr Met Met Ala
            95                 100                 105 ctc tgg gaa gag tgt aag ccc tgc ctg aaa c ag acc tgc atg aag ttc      567
Leu Trp Glu Glu Cys Lys Pro Cys Leu Lys G ln Thr Cys Met Lys Phe
        110                 115                 120 tac gca cgc gtc tgc aga agt ggc tca ggc c tg gtt ggc cgc cag ctt      615
Tyr Ala Arg Val Cys Arg Ser Gly Ser Gly L eu Val Gly Arg Gln Leu
    125                 130                 135 gag gag ttc ctg aac cag agc tcg ccc ttc t ac ttc tgg atg aat ggt      663
Glu Glu Phe Leu Asn Gln Ser Ser Pro Phe T yr Phe Trp Met Asn Gly
140                 145                 150                 155 gac cgc atc gac tcc ctg ctg gag aac gac c gg cag cag acg cac atg      711
Asp Arg Ile Asp Ser Leu Leu Glu Asn Asp A rg Gln Gln Thr His Met
                160                 165                 170 ctg gat gtc atg cag gac cac ttc agc cgc g cg tcc agc atc ata gac      759
Leu Asp Val Met Gln Asp His Phe Ser Arg A la Ser Ser Ile Ile Asp
            175                 180                 185 gag ctc ttc cag gac agg ttc ttc acc cgg g ag ccc cag gat acc tac      807
Glu Leu Phe Gln Asp Arg Phe Phe Thr Arg G lu Pro Gln Asp Thr Tyr
        190                 195                 200 cac tac ctg ccc ttc agc ctg ccc cac cgg a gg cct cac ttc ttc ttt      855
His Tyr Leu Pro Phe Ser Leu Pro His Arg A rg Pro His Phe Phe Phe
    205                 210                 215 ccc aag tcc cgc atc gtc cgc agc ttg atg c cc ttc tct ccg tac gag      903
Pro Lys Ser Arg Ile Val Arg Ser Leu Met P ro Phe Ser Pro Tyr Glu
220                 225                 230                 235 ccc ctg aac ttc cac gcc atg ttc cag ccc t tc ctt gag atg ata cac      951
Pro Leu Asn Phe His Ala Met Phe Gln Pro P he Leu Glu Met Ile His
                240                 245                 250
```

```
gag gct cag cag gcc atg gac atc cac ttc c ac agc ccg gcc ttc cag      999
Glu Ala Gln Gln Ala Met Asp Ile His Phe H is Ser Pro Ala Phe Gln
            255                 260                 265 cac ccg cca aca gaa ttc ata cga gaa ggc g ac gat gac cgg act gtg     1047
His Pro Pro Thr Glu Phe Ile Arg Glu Gly A sp Asp Asp Arg Thr Val
            270                 275                 280 tgc cgg gag atc cgc cac aac tcc acg ggc t gc ctg cgg atg aag gac     1095
Cys Arg Glu Ile Arg His Asn Ser Thr Gly C ys Leu Arg Met Lys Asp
285                 290                 295 cag tgt gac aag tgc cgg gag atc ttg tct g tg gac tgt tcc acc aac     1143
Gln Cys Asp Lys Cys Arg Glu Ile Leu Ser V al Asp Cys Ser Thr Asn
300                 305                 310                 315 aac ccc tcc cag gct aag ctg cgg cgg gag c tc gac gaa tcc ctc cag     1191
Asn Pro Ser Gln Ala Lys Leu Arg Arg Glu L eu Asp Glu Ser Leu Gln
            320                 325                 330 gtc gct gag agg ttg acc agg aaa tat aac g ag ctg cta aag tcc tac     1239
Val Ala Glu Arg Leu Thr Arg Lys Tyr Asn G lu Leu Leu Lys Ser Tyr
            335                 340                 345 cag tgg aag atg ctc aac acc tcc tcc ttg c tg gag cag ctg aac gag     1287
Gln Trp Lys Met Leu Asn Thr Ser Ser Leu L eu Glu Gln Leu Asn Glu
            350                 355                 360 cag ttt aac tgg gtg tcc cgg ctg gca aac c tc acg caa ggc gaa gac     1335
Gln Phe Asn Trp Val Ser Arg Leu Ala Asn L eu Thr Gln Gly Glu Asp
365                 370                 375 cag tac tat ctg cgg gtc acc acg gtg gct t cc cac act tct gac tcg     1383
Gln Tyr Tyr Leu Arg Val Thr Thr Val Ala S er His Thr Ser Asp Ser
380                 385                 390                 395 gac gtt cct tcc ggt gtc act gag gtg gtc g tg aag ctc ttt gac tct     1431
Asp Val Pro Ser Gly Val Thr Glu Val Val V al Lys Leu Phe Asp Ser
            400                 405                 410 gat ccc atc act gtg acg gtc cct gta gaa g tc tcc agg aag aac cct     1479
Asp Pro Ile Thr Val Thr Val Pro Val Glu V al Ser Arg Lys Asn Pro
            415                 420                 425 aaa ttt atg gag acc gtg gcg gag aaa gcg c tg cag gaa tac cgc aaa     1527
Lys Phe Met Glu Thr Val Ala Glu Lys Ala L eu Gln Glu Tyr Arg Lys
            430                 435                 440 aag cac cgg gag gag tga gatgtggatg ttgcttttgc a cctacgggg gcatctgagt  1585
Lys His Arg Glu Glu
    445 ccagctcccc ccaagatgag ctgcagcccc cagagagag ctctgcacgt c accaagtaa    1645 ccaggc                                                                1651

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
gtctttgcac gcctcggtca                                                   20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
attctggagt ctttgcacgc                                                   20
```

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
gtcttcatca tgcctccaat                                         20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
tctcccaggt cagcagcagc                                         20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tctggtcccc caggacctgc                                         20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
ggagctcatt gtctgagacc                                         20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
acttacttcc ctgattggac                                         20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
aatttcctta ttgacgtact                                         20

<210> SEQ ID NO 22
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 22
gtctttatct gtttcacccc                                          20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
gggcatcctc tttcttcttc                                          20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
atttagggca tcctctttct                                          20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ttccctggtc tcatttaggg                                          20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tgtctctgat tccctggtct                                          20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gggagctcct tcagctttgt                                          20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
cccagagggc catcatggtc                                          20
```

```
<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ctcttcccag agggccatca                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tcaggcaggg cttacactct                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gtgcgtagaa cttcatgcag                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ggcggccaac caggcctgag                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tggcggccaa ccaggcctga                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
actcctcaag ctggcggcca                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 35
agtagaaggg cgagctctgg 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ttcatccaga agtagaaggg 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
cagcagggag tcgatgcggt 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gctgccggtc gttctccagc 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
catccagcat gtgcgtctgc 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gacatccagc atgtgcgtct 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gtggtcctgc atgacatcca 20

<210> SEQ ID NO 42
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 42
aagtggtcct gcatgacatc                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ctggaagagc tcgtctatga                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
tgtcctggaa gagctcgtct                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gaacctgtcc tggaagagct                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ggaaagaaga agtgaggcct                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gggcatcaag ctgcggacga                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
```
ctcaaggaag ggctggaaca                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tctcaaggaa gggctggaac                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tgtatcatct caaggaaggg                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gctgtggaag tggatgtcca                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
attctgttgg cgggtgctgg                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tatgaattct gttggcgggt                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ggatctcccg gcacacagtc                                              20

<210> SEQ ID NO 55
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 55
cggatctccc ggcacacagt                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gtggagttgt ggcggatctc                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gtccttcatc cgcaggcagc                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
acagtccaca gacaagatct                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gagctcccgc cgcagcttag                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ggagggattc gtcgagctcc                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
atcttccact ggtaggactt                                               20
```

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
tgttgagcat cttccactgg                                          20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
agctgctcca gcaaggagga                                          20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
gctcgttcag ctgctccagc                                          20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ttgccagccg ggacacccag                                          20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
cgcagatagt actggtcttc                                          20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
accgtggtga cccgcagata                                          20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 68
cgagtcagaa gtgtgggaag                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gtgatgggat cagagtcaaa                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ggagacttct acagggaccg                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gccacggtct ccataaattt                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gcaaaagcaa catccacatc                                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tagagtgcag gatccagagc                                                    20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
attagttgca tgcaggagca                                                    20

<210> SEQ ID NO 75
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
agacagtttt attgaattag                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
cgagatagag ccactgtacg                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tgccaccacc cccgggtgat                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gttgttggtg gaacagtcca                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tgcttaccgg tgctttttgc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
acatctcact cctcccggtg                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
```
gaccctccaa gcgatcagct								20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
aaaaagagga ccctccaagc								20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
tgtgtcccct tttcacctgg								20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
attaccaatg gagcatggca								20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
caacatggcc aaaccccatg								20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
gcggcaggtc tccaggtctc								20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ttcccttcgg agagtagaga								20

<210> SEQ ID NO 88
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 88
tgcttgggaa atgcctgcaa                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
agctggatgc cagaaaggcc                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tggaagtagt ggaagccagg                                               20
```

ANTISENSE INHIBITION OF CLUSTERIN EXPRESSION

FIELD OF THE INVENTION

The present invention provides compositions and methods for modulating the expression of clusterin. In particular, this invention relates to compounds, particularly oligonucleotides, specifically hybridizable with nucleic acids encoding clusterin. Such compounds have been shown to modulate the expression of clusterin.

BACKGROUND OF THE INVENTION

Clusterin is an amphipathic glycoprotein that was first isolated from the male reproductive system (Bettuzzi et al., Biochem. J., 1989, 257, 293–296; O'Bryan et al., J. Clin. Invest., 1990, 85, 1477–1486). Subsequently, it has been shown that clusterin is ubiquitously distributed among tissues, having a wide range of biologic properties. Investigators from several disciplines, therefore, have isolated clusterin homologs under more than ten different names reviewed in (Bailey and Griswold, Mol. Cell. Endocrinol., 1999, 151, 17–23; Koch-Brandt and Morgans, Prog. Mol. Subcell. Biol., 1996, 16, 130–149; Meri and Jarva, Vox. Sang., 1998, 74, 291–302; Silkensen et al., Biochem. Cell. Biol., 1994, 72, 483–488).

The clusterin protein consists of two non-identical subunits of 34 kDa and 47 kDa, designated alpha and beta, respectively. Clusterin expression is induced almost exclusively as a result of cellular injury, death, or pathology.

Among its many roles, clusterin is a component of the soluble SCb-5 complement complex which is assembled in the plasma upon activation of the complement cascade (Choi et al., Mol. Immunol., 1989, 26, 835–840; Kirszbaum et al., Embo J., 1989, 8, 711–718; Murphy et al., Int. Immunol., 1989, 1, 551–554; Tschopp and French, Clin. Exp. Immunol., 1994, 97 Suppl 2, 11–14). Binding of clusterin has been shown to abolish the membranolytic potential of complement complexes and it has therefore been termed complement lysis inhibitor (CLI) (Jenne and Tschopp, Proc. Natl. Acad. Sci. U. S. A., 1989, 86, 7123–7127).

Further investigations of clusterin demonstrated that it circulates in plasma as a high density lipoprotein (HDL) complex which serves not only as an inhibitor of the lytic complement cascade, but as a regulator of lipid transport and local lipid redistribution (Jenne et al., J. Biol. Chem., 1991, 266, 11030–11036). In this capacity, clusterin isolated and characterized by de Silva et al. and was given the name Apolipoprotein J (ApoJ) (de Silva et al., Biochemistry, 1990, 29, 5380–5389; de Silva et al., J. Biol. Chem., 1990, 265, 13240–13247; de Silva et al., J. Biol. Chem., 1990, 265, 14292–14297). In these studies, clusterin (ApoJ) was shown to play a role in cholesterol transport in the liver and in the regulation of vascular smooth muscle cell differentiation (de Silva et al., J. Biol. Chem., 1990, 265, 13240–13247; Moulson and Millis, J. Cell. Physiol., 1999, 180, 355–364). A link between the modulation of HDL and complement activity is provided by studies by James et al. that characterize the association of a high density lipoprotein, NA1/NA2, with apolipoprotein A-I (ApoA-I). This novel protein NA1/NA2, was subsequently shown to be clusterin (James et al., Arterioscler. Thromb., 1991, 11, 645–652).

Clusterin has also been shown to participate in the cellular process of programmed cell death or apoptosis. Clusterin expression demarcates cells undergoing apoptosis (Buttyan et al., Mol. Cell. Biol., 1989, 9, 3473–3481) and in studies of the kidney, the onset of hydronephrosis following unilateral obstruction is associated with the increased expression of proteins encoded by the clusterin gene (Connor et al., Kidney Int., 1991, 39, 1098–1103). In both of these studies, clusterin is referred to by two other synonyms, sulfated glycoprotein-2 gene (SGP-2) and testosterone-repressed prostate message-2 (TRPM-2) (Buttyan et al., Mol. Cell. Biol., 1989, 9, 3473–3481; Connor et al., Kidney Int., 10 1991, 39, 1098–1103).

Sensibar et al. showed that cell death in the prostate, induced by tumor necrosis factor alpha, could be prevented by overexpressing clusterin. In these studies, transfection of LNCaP cells with any of four 21-mer antisense phosphorothioate oligonucleotides targeting the clusterin coding region resulted in an increase of cell death (Sensibar et al., Cancer Res., 1995, 55, 2431–2437).

Miyake et al. further demonstrated the role of clusterin as an anti-apoptotic gene in the Shionogi tumor model, a model used for the study of castration-induced apoptosis (Miyake et al., Cancer Res., 2000, 60, 170–176). In this model, androgen-dependent mammary carcinoma xenograft tumors in male mice undergo regression after castration but recur as apoptosis-induced tumors after one month. Using a phosphorothioate 21-mer antisense oligonucleotide to the mouse clusterin gene targeting the translation initiation site, Miyake et al. were able to show that treatment with the clusterin antisense oligonucleotide of mice with Shionogi tumors resulted in a more rapid onset of apoptosis and time to complete regresssion. There was also a significant delay of emergence of androgen-independent recurrent tumors compared to control oligonucleotide treated controls.

Using the same oligonucleotide in an experiment designed to test the efficacy of the oligonucleotide in combination with paclitaxel, Miyake et al. showed that the combination of antisense oligonucleotide and paclitaxel induced apoptosis in Shionogi tumors better than either agent alone. These studies suggest that the antisense oligonucleotide may be useful in enhancing the effects of cytotoxic chemotherapy in hormone-refractory prostate cancer (Miyake et al., Cancer Res., 2000, 60, 2547–2554).

Another antisense oligonucleotide, targeting the AUG initiation codon of clusterin was used to investigate the role of clusterin in endothelial cell activation. In these studies, it was shown that clusterin expression is upregulated upon laminar shear stress and that reduction of clusterin levels via antisense treatment increased endothelial cell activation (Urbich et al., Circulation, 2000, 101, 352–355).

The level of clusterin is increased in the hippocampus and frontal cortex of the brains of Alzheimer's disease patients. It is currently believed that clusterin, by binding to beta-amyloid, a protein known to aggregate in the brains of these patients, acts to link the progression of this disease to the complement system (Choi-Miura and Oda, Neurobiol. Aging, 1996, 17, 717–722).

Most recently, clusterin has been isolated as a KU70 binding protein. KU binding proteins (KUBs) are involved in DNA repair pathways. Clusterin (KUB1) was identified as an autoantigen in serum of patients with scleroderma-polymyositis syndrome and shown to dimerize with KUP80 to form an ATP dependent helicase and a regulatory component of a DNA dependent protein kinase (PRKDC) involved in double-strand break repair and V(D)J recombination (Yang et al., Nucleic Acids Res., 1999, 27, 2165–2174).

Clusterin is overexpressed in many disease states including neurodegenerative disorders, gliomas, retinitis pigmentosa and expression is induced in acute and chronic models of renal injury and disease, following ureter obstruction, ischemia/reperfusion, and atherosclerosis reviewed in (Silkensen et al., *Biochem. Cell. Biol.*, 1994, 72, 483–488). The pharmacological modulation of clusterin activity and/or expression may therefore be an appropriate point of therapeutic intervention in pathological conditions.

The expression of clusterin, or variants thereof, has been used as a means of differentiating normal versus abnormal cells in the study of male infertility. A method of assessing acrosomal status of sperm morphology comprising contacting a sperm sample with an immunologically reactive molecule which binds to one form of clusterin and not another is disclosed in WO 95/16916 (Baker and Murphy, 1995, ).

Currently, there are no known therapeutic agents which effectively inhibit the synthesis of clusterin and to date, investigative strategies aimed at modulating clusterin function have involved the use of antibodies, antisense oligonucleotides and chemical inhibitors.

There remains, however, a long felt need for additional agents capable of effectively inhibiting clusterin function.

Antisense technology is emerging as an effective means for reducing the expression of specific gene products and may therefore prove to be uniquely useful in a number of therapeutic, diagnostic, and research applications for the modulation of clusterin expression.

The present invention provides compositions and methods for modulating clusterin expression, including modulation of the alpha and/or beta subunits.

SUMMARY OF THE INVENTION

The present invention is directed to compounds, particularly antisense oligonucleotides, which are targeted to a nucleic acid encoding clusterin, and which modulate the expression of clusterin. Pharmaceutical and other compositions comprising the compounds of the invention are also provided. Further provided are methods of modulating the expression of clusterin in cells or tissues comprising contacting said cells or tissues with one or more of the antisense compounds or compositions of the invention. Further provided are methods of treating an animal, particularly a human, suspected of having or being prone to a disease or condition associated with expression of clusterin by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding clusterin, ultimately modulating the amount of clusterin produced. This is accomplished by providing antisense compounds which specifically hybridize with one or more nucleic acids encoding clusterin. As used herein, the terms "target nucleic acid" and "nucleic acid encoding clusterin" encompass DNA encoding clusterin, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of clusterin. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding clusterin. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding clusterin, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines.

Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, SO$CH_3$, O$NO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of clusterin is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding clusterin, enabling sandwich and other assays to easily be constructed to exploit this fact. Hybridization of the antisense oligonucleotides of the invention with a nucleic acid encoding clusterin can be detected by means known in the art. Such means may include conjugation of an enzyme to the oligonucleotide, radiolabelling of the oligonucleotide or any other suitable detection means. Kits using such detection means for detecting the level of clusterin in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion.

Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled*

*Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms,* Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include qaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 *In: Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, The Merck Manual of Diagnosis and Therapy, 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499–2506 and 46–49., respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., Nucleic Acids Research, 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., J. Med. Chem., 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3' phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 9, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHC_{13}$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% ET$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1'300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites

2'-(Dimethylaminooxyethoxy) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O²-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl)thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the reaction mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 9, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl]-5-methyl uridine

To 0.5 g (1.3 mmol) of 2'-O-[2(2-N,N-dimethylaminoethoxy)ethyl]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$ET_3N$ (20:1, v/v, with 1% triethylamine) gives the title compound.

5'-O-Dimethoxytrityl-2'-O-[2(2-N,N-dimethylaminoethoxy)ethyl]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2
Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos., 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA); Synthesis, Properties and Potential Applications, *Bioorganic & Medicinal Chemistry*, 1996, 4, 5–23. They may also be prepared in accordance with U.S.

Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphormidite for the DNA portion and 5'-dimethoxytrityl-2'-O-ethyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)]Chimeric Phosphorothioate Oligonucleotides

[2'-O-(2-methoxyethyl)]—[2'-deoxy]—[-2'-O-(methoxyethyl)]chimeric phosphorothioate oligonucleotides were prepared as per the procedure above for the 2'-O-methyl chimeric oligonucleotide, with the substitution of 2'-O-(methoxyethyl)amidites for the 2'-O-methyl amidites.

[2'-O-(2-Methoxyethyl)Phosphodiester]—[2'-deoxy Phosphorothioate]—[2'-O-(2-Methoxyethyl) Phosphodiester]Chimeric Oligonucleotides

[2'-O-(2-methoxyethyl phosphodiester]—[2'-deoxy phosphorothioate]—[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U. S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Clusterin Expression

Antisense modulation of clusterin expression can be assayed in a variety of ways known in the art. For example, clusterin mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F.M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F.M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of clusterin can be quantitated in a variety of ways well known in the art, such as immunoprecipitation, Western blot analysis (immunoblotting), ELISA or fluorescence-activated cell sorting (FACS). Antibodies directed to clusterin can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F.M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F.M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F.M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F.M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F.M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY $_{96}$™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Clusterin mRNA Levels

Quantitation of clusterin mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 µL PCR cocktail (1×TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Probes and primers to human clusterin were designed to hybridize to a human clusterin sequence, using published sequence information (GenBank accession number M64722, incorporated herein as SEQ ID NO:3). For human clusterin the PCR primers were: forward primer: TCCG-TACGAGCCCCTGAA (SEQ ID NO: 4) reverse primer: TGAGCCTCGTGTATCATCTCAAG (SEQ ID NO: 5) and the PCR probe was: FAM-TCCACGCCATGTTCCAGCCCT-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: CAACGGATTTGGTCGTATTGG (SEQ ID NO: 7) reverse primer: GGCAACAATATCCACTTTACCAGAGT (SEQ ID NO: 8) and the PCR probe was: 5' JOE-CGCCTGGTCACCAGGGCTGCT-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of Clusterin mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human clusterin, a human clusterin specific probe was prepared by PCR using the forward primer TCCGTACGAGCCCCTGAA (SEQ ID NO: 4) and the reverse primer TGAGCCTCGTGTATCATCTCAAG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human Clusterin Expression by Chimeric Phosphorothioate Oligonucleotides Having 2'-MOE Wings and a Deoxy Gap In accordance with the present invention, a series of oligonucleotides were designed to target different regions of the human clusterin RNA, using published sequences (GenBank accession number M64722, incorporated herein as SEQ ID NO: 3, GenBank accession number L00974, incorporated herein as SEQ ID NO: 10, GenBank accession number M63377, incorporated herein as SEQ ID NO: 11, GenBank accession number M63376, incorporated herein as SEQ ID NO: 12, and GenBank accession number M25915, incorporated herein as SEQ ID NO: 13). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human clusterin mRNA levels by quantitative real-time PCR as described in other examples herein. Data are averages from two experiments. If present, "N.D." indicates "no data".

TABLE 1

Inhibition of human clusterin mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 129045 | 5'UTR | 3 | 18 | gtctttgcacgcctcggtca | 64 | 14 |
| 129046 | 5'UTR | 3 | 26 | attctggagtctttgcacgc | 64 | 15 |
| 129047 | Start Codon | 3 | 44 | gtcttcatcatgcctccaat | 68 | 16 |
| 129048 | Coding | 3 | 82 | tctcccaggtcagcagcagc | 67 | 17 |
| 129049 | Coding | 3 | 106 | tctggtcccccaggacctgc | 46 | 18 |
| 129050 | Coding | 3 | 127 | ggagctcattgtctgagacc | 59 | 19 |
| 129052 | Coding | 3 | 154 | acttacttccctgattggac | 77 | 20 |
| 129053 | Coding | 3 | 171 | aatttccttattgacgtact | 68 | 21 |

TABLE 1-continued

Inhibition of human clusterin mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 129054 | Coding | 3 | 206 | gtctttatctgtttcacccc | 85 | 22 |
| 129055 | Coding | 3 | 286 | gggcatcctctttcttcttc | 64 | 23 |
| 129056 | Coding | 3 | 291 | atttagggcatcctctttct | 31 | 24 |
| 129057 | Coding | 3 | 303 | ttccctggtctcatttaggg | 68 | 25 |
| 129058 | Coding | 3 | 312 | tgtctctgattccctggtct | 79 | 26 |
| 129059 | Coding | 3 | 329 | gggagctccttcagctttgt | 49 | 27 |
| 129060 | Coding | 3 | 364 | cccagagggccatcatggtc | 45 | 28 |
| 129061 | Coding | 3 | 369 | ctcttcccagagggccatca | 36 | 29 |
| 129062 | Coding | 3 | 385 | tcaggcagggcttacactct | 70 | 30 |
| 129063 | Coding | 3 | 412 | gtgcgtagaacttcatgcag | 60 | 31 |
| 129064 | Coding | 3 | 448 | ggcggccaaccaggcctgag | 42 | 32 |
| 129065 | Coding | 3 | 449 | tggcggccaaccaggcctga | 32 | 33 |
| 129066 | Coding | 3 | 460 | actcctcaagctggcggcca | 67 | 34 |
| 129067 | Coding | 3 | 487 | agtagaagggcgagctctgg | 63 | 35 |
| 129068 | Coding | 3 | 497 | ttcatccagaagtagaaggg | 41 | 36 |
| 129069 | Coding | 3 | 522 | cagcagggagtcgatgcggt | 60 | 37 |
| 129070 | Coding | 3 | 538 | gctgccggtcgttctccagc | 51 | 38 |
| 129071 | Coding | 3 | 556 | catccagcatgtgcgtctgc | 69 | 39 |
| 129072 | Coding | 3 | 558 | gacatccagcatgtgcgtct | 55 | 40 |
| 129073 | Coding | 3 | 570 | gtggtcctgcatgacatcca | 62 | 41 |
| 129074 | Coding | 3 | 572 | aagtggtcctgcatgacatc | 41 | 42 |
| 129075 | Coding | 3 | 609 | ctggaagagctcgtctatga | 67 | 43 |
| 129076 | Coding | 3 | 613 | tgtcctggaagagctcgtct | 69 | 44 |
| 129077 | Coding | 3 | 618 | gaacctgtcctggaagagct | 68 | 45 |
| 129078 | Coding | 3 | 695 | ggaaagaagaagtgaggcct | 44 | 46 |
| 129079 | Coding | 3 | 726 | gggcatcaagctgcggacga | 65 | 47 |
| 129080 | Coding | 3 | 780 | ctcaaggaagggctggaaca | 81 | 48 |
| 129081 | Coding | 3 | 781 | tctcaaggaagggctggaac | 81 | 49 |
| 129082 | Coding | 3 | 788 | tgtatcatctcaaggaaggg | 38 | 50 |
| 129083 | Coding | 3 | 825 | gctgtggaagtggatgtcca | 48 | 51 |
| 129084 | Coding | 3 | 853 | attctgttggcgggtgctgg | 50 | 52 |
| 129085 | Coding | 3 | 858 | tatgaattctgttggcgggt | 36 | 53 |
| 129086 | Coding | 3 | 898 | ggatctcccggcacacagtc | 68 | 54 |
| 129087 | Coding | 3 | 899 | cggatctcccggcacacagt | 70 | 55 |
| 129088 | Coding | 3 | 911 | gtggagttgtggcggatctc | 69 | 56 |

TABLE 1-continued

Inhibition of human clusterin mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 129089 | Coding | 3 | 933 | gtccttcatccgcaggcagc | 56 | 57 |
| 129090 | Coding | 3 | 972 | acagtccacagacaagatct | 49 | 58 |
| 129092 | Coding | 3 | 1014 | gagctcccgccgcagcttag | 22 | 59 |
| 129093 | Coding | 3 | 1027 | ggagggattcgtcgagctcc | 55 | 60 |
| 129094 | Coding | 3 | 1088 | atcttccactggtaggactt | 50 | 61 |
| 129095 | Coding | 3 | 1096 | tgttgagcatcttccactgg | 62 | 62 |
| 129096 | Coding | 3 | 1118 | agctgctccagcaaggagga | 46 | 63 |
| 129097 | Coding | 3 | 1126 | gctcgttcagctgctccagc | 43 | 64 |
| 129098 | Coding | 3 | 1153 | ttgccagccgggacacccag | 72 | 65 |
| 129099 | Coding | 3 | 1187 | cgcagatagtactggtcttc | 61 | 66 |
| 129100 | Coding | 3 | 1199 | accgtggtgacccgcagata | 73 | 67 |
| 129101 | Coding | 3 | 1221 | cqagtcagaagtqtgggaag | 24 | 68 |
| 129102 | Coding | 3 | 1280 | gtgatgggatcagagtcaaa | 38 | 69 |
| 129103 | Coding | 3 | 1305 | ggagacttctacagggaccg | 63 | 70 |
| 129104 | Coding | 3 | 1337 | gccacggtctccataaattt | 70 | 71 |
| 129106 | 3'UTR | 3 | 1403 | gcaaaagcaacatccacatc | 74 | 72 |
| 129107 | 3'UTR | 3 | 1550 | tagagtgcaggatccagagc | 71 | 73 |
| 129108 | 3'UTR | 3 | 1605 | attagttgcatgcaggagca | 71 | 74 |
| 129109 | 3'UTR | 3 | 1620 | agacagttttattgaattag | 11 | 75 |
| 129118 | Intron | 10 | 2819 | cgagatagagccactgtacg | 44 | 76 |
| 129119 | Intron | 10 | 4646 | tqccaccaccccqqqtqat | 13 | 77 |
| 129091 | Intron-Exon Junction | 10 | 5849 | gttgttggtggaacagtcca | 40 | 78 |
| 129120 | Intron-Exon Junction | 10 | 7384 | tgcttaccggtgcttttgc | 46 | 79 |
| 129105 | Intron-Exon Junction | 10 | 7600 | acatctcactcctcccggtg | 70 | 80 |
| 129121 | 3'UTR | 10 | 7855 | gaccctccaagcgatcagct | 20 | 81 |
| 129122 | 3'UTR | 10 | 7863 | aaaaagaggaccctccaagc | 39 | 82 |
| 129115 | Intron-Exon Junction | 11 | 322 | tgtgtcccttttcacctgg | 54 | 83 |
| 129116 | Intron | 11 | 445 | attaccaatggagcatggca | 43 | 84 |
| 129117 | Intron | 11 | 810 | caacatggccaaaccccatg | 55 | 85 |
| 129112 | Intron | 12 | 1766 | gcggcaggtctccaggtctc | 43 | 86 |

TABLE 1-continued

Inhibition of human clusterin mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 129110 | Intron | 12 | 4813 | ttcccttcggagagtagaga | 44 | 87 |
| 129113 | Intron | 12 | 5848 | tgcttgggaaatgcctgcaa | 34 | 88 |
| 129114 | Intron | 12 | 6936 | agctggatgccagaaaggcc | 40 | 89 |
| 129111 | 5'UTR | 13 | 39 | tggaagtagtggaagccagg | 11 | 90 |

As shown in Table 1, SEQ ID NOs 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 69, 70, 71, 72, 73, 74, 76, 78, 79, 80, 82, 83, 84, 85, 86, 87, 88 and 89 demonstrated at least 30% inhibition of human clusterin expression in this assay and are therefore preferred. The target sites to which these preferred sequences are complementary are herein referred to as "active sites" and are therefore preferred sites for targeting by compounds of the present invention.

Example 16
Western Blot Analysis of Clusterin Protein Levels

Western blot analysis (immunoblot analysis) is carried out using standard methods. Cells are harvested 16–20 h after oligonucleotide treatment, washed once with PBS, suspended in Laemnli buffer (100 ul/well), boiled for 5 minutes and loaded on a 16% SDS-PAGE gel. Gels are run for 1.5 hours at 150 V, and transferred to membrane for western blotting. Appropriate primary antibody directed to clusterin is used, with a radiolabelled or fluorescently labeled secondary antibody directed against the primary antibody species. Bands are visualized using a PHOSPHORIMAGER™ (Molecular Dynamics, Sunnyvale Calif.).

---

What is claimed is:

1. A compound up to 50 nucleobases in length comprising at least an 8-nucleobase portion of SEQ ID NO: 18, 19, 20, 21, 22, 23, 24, 25, 26, 27, 28, 29, 30, 31, 32, 33, 34, 35, 36, 38, 39, 40, 41, 42, 43, 44, 45, 46, 48, 49, 50, 51, 52, 53, 54, 55, 56, 57, 58, 60, 61, 62, 65, 66, 69, 70, 71, 72, 73, 74, 76, 78, 79, 80, 82, 83, 84, 85, 86, 87, 88 or 89 which inhibits the expression of human clusterin (SEQ ID NO: 3).

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 2 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of human clusterin in cells or tissues comprising contacting said cells or tissues in vitro with the antisense compound of claim 1 so that expression of human clusterin is inhibited.

* * * * *

UNITED STATES PATENT AND TRADEMARK OFFICE
CERTIFICATE OF CORRECTION

PATENT NO. : 6,383,808 B1
DATED : May 7, 2002
INVENTOR(S) : Susan M. Freier

It is certified that error appears in the above-identified patent and that said Letters Patent is hereby corrected as shown below:

Title page,
Item [12], delete "Monia et al." and substitute -- Freier --;
Item [75], Inventors, delete "Brett P. Monia, La Costa;";
Item [56], References Cited, OTHER PUBLICATIONS,
"Kirszbaum" reference, delete "cloniing" and insert -- cloning --;

Column 96,
Line 37, delete "2" and insert -- 1 --.

Signed and Sealed this

Second Day of May, 2006

JON W. DUDAS
*Director of the United States Patent and Trademark Office*